United States Patent [19]

Boyer

[11] Patent Number: 4,961,890
[45] Date of Patent: Oct. 9, 1990

[54] METHOD OF PREPARING COMTROLLED RELEASE FENOFIBRATE

[75] Inventor: Jean-Francois Boyer, Houdan, France

[73] Assignee: Ethypharm, Houdan, France

[21] Appl. No.: 256,836

[22] Filed: Oct. 12, 1988

Related U.S. Application Data

[62] Division of Ser. No. 83,409, Aug. 10, 1987, Pat. No. 4,800,079.

[30] Foreign Application Priority Data

Aug. 8, 1986 [FR] France .................................. 86 11540

[51] Int. Cl.$^5$ .......................... B28B 11/06; A61K 9/22
[52] U.S. Cl. .................................... 264/113; 264/114; 264/121; 264/122; 264/123; 264/131; 424/439; 424/471; 424/479; 424/482; 424/490; 427/412.1
[58] Field of Search .................. 264/5, 6, 7, 122, 109, 264/113, 123, 125, 114, 131, 121; 424/482, 490, 439, 471, 479, 459, 440, 419, 470; 427/412, 416; 514/537, 543

[56] References Cited

U.S. PATENT DOCUMENTS

| | | | |
|---|---|---|---|
| 2,154,185 | 4/1939 | Robie | 264/123 |
| 3,143,473 | 8/1964 | Hennessen et al. | 424/490 |
| 3,836,618 | 9/1974 | Stevens | 264/123 |
| 3,922,338 | 11/1975 | Estevenel et al. | 264/113 |
| 4,011,061 | 3/1977 | Forseen et al. | 427/412.1 |
| 4,025,613 | 5/1977 | Guy et al. | 264/113 |
| 4,259,315 | 3/1981 | Lippmann et al. | 424/490 |
| 4,684,516 | 8/1987 | Bhutani | 264/123 |
| 4,721,619 | 1/1988 | Panoz et al. | 424/459 |
| 4,786,509 | 11/1988 | Chang et al. | 424/490 |
| 4,800,079 | 1/1989 | Boyer | 424/482 |
| 4,814,354 | 3/1989 | Ghebre et al. | 424/440 |
| 4,837,031 | 6/1989 | Denton | 424/490 |
| 4,859,703 | 8/1989 | Krause . | |

*Primary Examiner*—James Lowe
*Assistant Examiner*—Mathieu Varget
*Attorney, Agent, or Firm*—Sughrue, Mion, Zinn, Macpeak & Seas

[57] ABSTRACT

A process for preparing a controlled release medicine containing fenofibrate in an intermediate layer in the form of cyrstalline microparticles included within pores of an inert matrix prepared by a process involving the sequential steps of dampening said inert core with a solution based on said biner, then projecting said fenofibrate microparticles in a single layer onto said dampened core, and thereafter drying before said solution based on said binder dissolves said fenofibrate microparticles and repeating said three steps in sequence until said intermediate layer is formed.

11 Claims, No Drawings

METHOD OF PREPARING COMTROLLED RELEASE FENOFIBRATE

This is a Division of application Ser. No. 07/083,409 filed Aug. 10, 1987, now U.S. Pat. No. 4,800,079.

The present invention relates to a medicine based on fenofibrate, and also to a method of preparing it.

BACKGROUND OF THE INVENTION

It is recalled that fenofibrate is isopropyl para-(4-chlorobenzoyl)-pehnoxyisobutyrate. In the present application, the term "fenofibrate and its derivatives" is used to designate compounds having formula I:

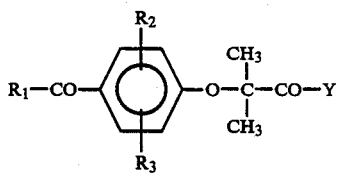

in which:

$R_1$ represents a phenyl group or a phenyl group substituted by one or more —$CH_3$, $CF_3$ or by halogens (in particular fluorine, chlorine, or bromine);

$R_2$ and $R_3$ independently represent a hydrogen atom or a halogen atom (preferably fluorine, chlorine, or bromine), an alkyl or an alkoxy group having 1 to 5 C or one of the following groups: —$CF_3$, —$SCH_3$, —$SOCH_3$, —$SO_2CH_3$, or —OH; and Y represents one of the following groups: —OH; inferior alkoxy, preferably in $C_1$-$C_4$; —$NR_4R_5$; —$NHCH_2CH_2NR_4R_5$; or —O—alkylene—$NR_4R_5$, with the alkylene having, in particular, two to six atoms of carbon, and with $R_4$ and $R_5$ being identical or different and each representing a hydrogen atom or one of the following groups: $C_1$-$C_5$ alkyl, $C_3$-$C_7$ and preferably $C_5$-$C_6$ cycloalkyl; aryl or aryl substituted on the aromatic residue by one or more halogen, methyl, or —$CF_3$ groups; or else $R_4$ and $R_5$ constitute, together with the nitrogen atom to which they are connected, one of the following groups: either an n-heterocyclic group having 5 to 7 vertices capable of enclosing a second hetero-atom selected from N, O, and S, and capable of being substituted; or else an amide residue derived from lysine or cysteine.

Naturally, the expression "fenofibrate and its derivatives" also covers the salts that can be obtained from compounds of formula I by adding pharmaceutically acceptable acids.

Fenofibrate is used in the treatment of adult endogenous hyperlipidaemia, hypercholesterolaemia, and hypertrigylceridaemia. Thus, in an adult being treated with 300 to 400 mg per day of fenofibrate, there can be observed a 20% to 25% reduction in cholesterolaemia and a 40% to 50% reduction in triglyceridaemia.

The unaltered substance is not found in plasma. The major plasmatic metabolite is fenofibric acid.

On average, the maximum concentration in plasma is reached five hours after taking the medicine. The average concentration in plasma is about 50 micrograms/ml for a dose of 300 mg of fenofibrate per day. This level is stable throughout continuous treatment.

Fenofibric acid is strongly bound to plasmatic albumin and can displace antivitamins K from protein fixing sites and potentialize their anticoagulant effect.

The half-life for eliminating fenofibric acid from plasma is about twenty hours.

Under these conditions, it will be understood that there is no need to take it more than once a day.

It has been observed that fenofibrate has poor solubility in aqueous liquids, thereby giving rise to non-uniform absorption in the digestive tube, and in accordance with the present invention a galenical preparation has been devised which considerably improves absorption by the digestive tube.

SUMMARY OF THE INVENTION

The present invention provides a medicine based on fenofibrate and in the form of granules, each granule comprising an inert core, a layer based on fenofibrate, and a protective layer. In the layer based on fenofibrate, the fenofibrate is present in the form of crystalline microparticles of dimensions not greater than 30 microns, and preferably less than 10 microns.

In accordance with the present invention, this structure is obtained by a method including a step of projecting a damp and sticky outer layer onto the inert cores, followed by a step of projecting fenofibrate microparticles onto the damp layer with the dampness being rapidly evaporated in order to prevent it from dissolving the fenofibrate microparticles while never-the-less fixing said fenofibrate microparticles onto the cores, with said two steps being repeated until a sufficient quantity of fenofibrate has been fixed onto the cores.

The damp and sticky layer may advantageously be constituted by a solution of a polymer in alcohol or by an aqueous suspension of the polymer, and the alcohol solution may be prepared using alcohols which are commonly used in pharmacology.

MORE DETAILED DESCRIPTION

There follows a description, by way of example, of the manufacture of one embodiment of a medicine in accordance with the present invention.

Inert grains for forming the inert cores are prepared in conventional manner. For example, each grain may be a sucrose crystal having a diameter of 0.3 mm. A suspension of maize starch is sprayed onto the crystals, the suspension comprising 27% by weight of maize starch in a hot sugar solution (prepared, for example, by dissolving 73 kg of sugar in 32 kg of water: 27 kg starch, 73 kg sugar, 32 kg water). The sugar solution is projected at 50° C. into a turbine which is itself heated to 50° C. The quantity projected is adjusted so that the diameter of each grain increases from 0.3 mm to 0.6 mm, with the grain having about 25% by weight starch and about 75% sucrose, once the water has evaporated from the sugar solution.

Thereafter, the inert cores are rotated in a turbine and they are dampened with an alcohol solution containing 12.5% by weight of a methyacrylic polymer (95° alcohol). The grains become damp and sticky. Fenofibrate powder is then projected onto them, with the powder being obtained by crushing fenofibrate crystals until microparticles are obtained. A typical powder has the following partical size distribution:

| | |
|---|---|
| 100% | <30 microns |
| 99.5% | <20 microns |
| 98% | <10 microns |
| 88% | <5 microns |

The grains are then immediately dried very rapidly in order to prevent the alcohol from having enough time to dissolve the fenofibrate (a flow of air is passed through the turbine). This avoids destroying the microparticulate structure which offers a considerable area for encouraging absorption. A single thickness of microparticles is thus deposited on the sticky grain where the microparticles are fixed by adherence. The operations of dampening-projecting-drying may be performed in about one or two minutes. These operations of dampening the core and projecting microparticles are repeated until all of the powder has been incorporated.

Finally, a protective coating is applied, e.g. a thin layer of methacrylic polymer, representing about 1% by weight of each granule.

Granules obtained in this way are put into capsules, with a dose of 250 mg of fenofibrate per capsule.

The fenofibrate layer structure is similar to that of a sponge, with the pores containing microparticles of fenofibrate. The sponge is constituted by a binder which is soluble in an aqueous medium: methacrylate or polyvinylpyrolidone. Once the binder has dissolved, the microparticles of fenofibrate are released and can present their entire areas to the process of absorption in the intestinal aqueous medium.

One example of formulation is as follows:

| fenofibrate | 400 kg |
|---|---|
| inert grains | 110 kg (sugar and/or starch) |
| polyvinylpyrolidone and/or methacrylate | 20 kg |

Of the last 20 kg, about 5 kg are used for making the protective envelope (about 1% of the total weight) and the remainder (about 15 kg) is used for binding the microparticles of fenofibrate, with alcohol being used temporarily as the solvent.

The quantity of binder is determined so that at least 65% of the fenofibrate is released in one hour in a water based liquid medium.

This fraction can be measured as follows: the contents of a capsule is placed in a flask containing 35 ml of a medium having a pH of 1.5. The flask is stirred at 30 rpm and at 37° C. After stirring for one hour, the percentage of fenofibrate that has been released from the galenical preparation in accordance with the invention is greater than 65%.

Composition of the medium:
118 ml normal hydrochloric acid
84 ml solution of normal sodium hydroxide distilled water: enough to obtain 1000.0 ml of medium.

The pH of the medium lies between 1.45 and 1.55.

Medicines in accordance with the invention have also shown reductions in variability of blood concentrations both inter and intra patient (i.e. on the same patient or between different patients).

We claim:

1. A method for preparing a medicine involving a controlled release of fenofibrate in aqueous medium, said medicine being in the form of a granule that comprises an inert core in its center, a protective outer coating and an intermediate layer based on fenofibrate, said process comprising forming said intermediate layer on said inert core by performing in a time duration of the order of one or two minutes three sequential steps (i), (ii) and (iii) as follows:
   (i) dampening said inert core with a solution based on a binder comprising a solvent selected from the group consisting of water and alcohols,
   (ii) then projecting onto said dampened core in a single layer fenofibrate crystalline microparticles that have diameters less than 30 microns,
   (iii) and thereafter drying before said solution based on said binder dissolves said fenofibrate microparticles, and repeating said three steps in sequence until said intermediate layer is formed so that said fenofibrate microparticles therein are included in the pores of an inert matrix constituted by said binder.

2. A method according to claim 1 wherein said binder constituting said inert matrix is a substance selected from the group consisting of methacrylic polymers, polyvinylpyrolidone, mixtures of methacrylic polymers and polyvinylpyrolidone cellulose derivatives and polyethylene glycols.

3. A method according to claim 1 wherein said inert core is prepared by spraying an aqueous sugar solution containing a starch suspension at about 50° C. onto sugar crystals having a diameter of about 0.3 mm until their diameter reaches about 0.6 mm.

4. A method according to claim 3 wherein said sugar in said crystals having a diameter of about 0.3 mm is selected from the sugar group consisting of glucose, sucrose, lactose and their equivalents.

5. A method according to claim 3 wherein said starch in said suspension is maize starch.

6. A method according to claim 3 wherein said inert core comprises about 25% by weight starch and about 75% by weight sugar.

7. A method according to claim 1 wherein said protective outer layer is made of a substance selected from the group consisting of methacrylic polymers, polyvinylpyrolidone, and mixtures of methacrylic polymers and polyvinylpyrolidone, and cellulose derivatives and polyethylene glycols.

8. A method according to claim 1 wherein said protective outer layer represents about 1% by weight of said granule.

9. A method according to claim 1 wherein said process is conducted in a turbine, and said drying operation is carried out with the help of an air flow.

10. A method according to claim 1 wherein said process is repeated until said intermediate layer contains a quantity of said binder such that the quantity of fenofibrate released in one hour in an aqueous medium is greater than 65%.

11. A method according to claim 3 wherein said sugar in said aqueous solution is selected from the sugar group consisting of glucose, sucrose, lactose and their equivalents.

* * * * *